(12) United States Patent
Furiya et al.

(10) Patent No.: US 6,912,047 B2
(45) Date of Patent: Jun. 28, 2005

(54) APPARATUS, METHOD AND SYSTEM FOR INSPECTING A FASTENER

(75) Inventors: Keven I. Furiya, Chicago, IL (US); Jeffrey M. Hansen, Chicago, IL (US); Scott W. Lea, Chicago, IL (US); Charles M. Richards, Chicago, IL (US)

(73) Assignee: The Boeing Company, Chicago, IL (US)

( * ) Notice: Subject to any disclaimer, the term of this patent is extended or adjusted under 35 U.S.C. 154(b) by 398 days.

(21) Appl. No.: 10/319,122

(22) Filed: Dec. 13, 2002

(65) Prior Publication Data

US 2004/0114133 A1 Jun. 17, 2004

(51) Int. Cl.[7] .............................................. G01N 21/00
(52) U.S. Cl. ................................................... 356/237.1
(58) Field of Search .......................... 356/237.1–237.5, 356/614; 250/223 R, 559.26, 559.45

(56) References Cited

U.S. PATENT DOCUMENTS

| | | | |
|---|---|---|---|
| 3,072,093 A | * | 1/1963 | Lanius, Jr. ...................... 411/8 |
| 4,457,622 A | * | 7/1984 | Kato et al. ................... 209/586 |
| 4,855,592 A | * | 8/1989 | Ogura ...................... 356/237.1 |
| 5,132,802 A | | 7/1992 | Osthues et al. |
| 5,288,991 A | | 2/1994 | King et al. |
| 5,892,241 A | | 4/1999 | Moriya |
| 6,072,583 A | * | 6/2000 | Kellner ....................... 356/614 |
| 6,606,252 B1 | * | 8/2003 | Snider ........................ 361/777 |
| 6,762,426 B1 | * | 7/2004 | Gilliam ................. 250/559.12 |

FOREIGN PATENT DOCUMENTS

JP        2000218338 A  *  8/2000

* cited by examiner

Primary Examiner—Hoa Q. Pham
(74) Attorney, Agent, or Firm—Alston & Bird LLP (57) ABSTRACT

The apparatus, method and system for inspecting a fastener installed in a structure includes the illumination of a fastener and a portion of the structure surrounding the fastener, the detection of the light reflected from the fastener and the portion of the structure surrounding the fastener, the analysis of the reflected light, and the definition of at least one inspection criteria. The structure has a coating that reflects light of a predefined wavelength differently than the fastener. As such, the light that illuminates the fastener and the structure surrounding the fastener has a wavelength within the predefined range. The light reflected from the fastener and the portion of the structure surrounding the fastener is then detected and analyzed to determine an interface between exposed surfaces of the fastener and the coating. Based upon the detected interface, at least one inspection criteria may then be defined.

52 Claims, 3 Drawing Sheets

APPARATUS, METHOD AND SYSTEM FOR INSPECTING A FASTENER

BACKGROUND OF THE INVENTION

This invention relates to the inspection of fasteners installed in structures, and, in particular, to the inspection of fasteners by analyzing light reflected from a fastener and the portion of the structure surrounding the fastener that reflect light of a predetermined wavelength differently than a coating on the structure.

The fasteners that hold structures together, particularly those structures that are subject to significant dynamic forces and/or pressure over their lifetime, such as aircraft, spacecraft, bridges, vehicles, buildings, ships, train bodies, material handling and storage equipment, ladders, scaffolding, and others, must be properly secured in order to ensure that the structure will perform as intended over its lifetime. For example, fasteners are used to hold together various segments of the structure, such as layers of the structure or overlapping portions of the structure, and/or to attach any type of component to the structure.

For instance, in the aerospace industry, fasteners, such as rivets, are commonly utilized to hold together various segments of an aircraft, such as the wing panels, the fuselage segments, and the wing and tail spar segments. Typically, to comply with aerodynamic requirements, the portion of the fastener that extends beyond the outer surface of the structure is removed such that the fastener is substantially flush with the outer surface of the structure. To remove the portion of the fastener that extends beyond the outer surface of the structure, that portion of the fastener is typically shaved by manual means, automated means, or a combination of both.

An automated fastener installation system, for example, may include both the fastener installation means and the fastener shaving means. As such, the fastener installation system typically has a transfer head on which both the fastener installation means and the fastener shaving means are located. The transfer head can then move with respect to the surface between the installation position, where the installation means is aligned with the area of the structure to receive the fastener, and the shaving position, where the shaving means is aligned with the installed fastener. Once the fastener is shaved, the transfer head moves to align the installation means with the next area of the structure to receive a fastener. One example of such a fastener installation system is the 777 Automated Wing Assembly System, commercially available from the General Electro Mechanical Corporation.

Installing and shaving the fastener, however, produces debris and excess fluid that accumulates on the outer surface of the structure. For instance, when the fastener is installed in the structure, pieces of the structure may be displaced, and may accumulate on the outer surface of the structure. In addition, in order to more easily shave the portion of the fastener that extends beyond the outer surface of the structure, at least one type of lubricant may be sprayed on the fastener. As the lubricant is sprayed on the fastener, and as the fastener is shaved, the lubricant and the shaved pieces of the fastener may also accumulate on the outer surface of the structure.

After an installed fastener is shaved, it is typically inspected to determine whether the fastener is shaved properly. For instance, if the fastener is shaved properly, it is flush with the outer surface of the structure. If, however, the fastener is not shaved enough, i.e., the fastener is high, then a portion of the fastener will extend beyond the outer surface of the structure. In this situation, the fastener may be manually shaved until it is flush with the outer surface of the structure. Alternatively, the automated shaving means may be readjusted and repositioned to align the shaving means with the fastener and to shave more of the fastener. In addition, if the fastener is shaved too much, i.e., the fastener is low, then a portion of the structure surrounding the fastener will also be shaved, which creates a recessed area in the structure that may negatively affect the stability and/or the aerodynamics of the structure. In this situation, extensive rework is typically required to repair the recessed area by filling and blending the area in preparation for a new fastener to be installed. In certain applications, however, such as in aircraft wings, a recessed area that is over 0.005 inches deep from the top of the coating cannot be repaired because the size of the recessed area is too large to ensure structural integrity, even if the recessed area is filled and blended. As such, at least the segment of wing with the recessed area must be replaced, and the fastener(s) reinserted.

The new fastener is then shaved and subsequently inspected. Because a low fastener requires significantly more rework than a high fastener, it is preferable to adjust the shaving means to produce a high fastener, instead of risking shaving off too much of the fastener.

The different parts of the structure in which the fasteners are installed typically have varying rigidities. For instance, the body of an aircraft may be more rigid than the wings of the aircraft. As such, the rigidity of the particular part of the structure in which a fastener is installed may affect the amount of the fastener that is shaved. When the shaving means of the fastener installation system applies the force to the fastener that is required to shave the fastener, the underlying structure may maintain its position if it is sufficiently rigid, or it may move slightly away from the shaving means if it is less rigid. Therefore, if the structure moves slightly away from the shaving means, it will not be shaved enough and will have to be re-shaved at a later time.

The shaved fasteners are typically inspected visually, after removing the fastener installation system from the structure. Fastener inspectors may then run their fingers over the installed fasteners and, if their fingers catch on the fastener or catch in a recessed area, then the fastener is identified as a high or low fastener, respectively. The fastener inspectors may also use a dial gauge during their visual inspection. The dial gauge is a hand held mechanical instrument used to measure linear displacement in the range of thousandths or tens of thousandths of an inch. This inspection process is subject to human error because the inspectors are dependent upon their sense of feel and/or a manual instrument for identification of improperly shaved fasteners. In addition, the visual inspection process is time and labor consuming, and therefore, expensive. Furthermore, some areas of the structure may be difficult and/or dangerous for the inspector to physically reach. For example, for particular aircraft parts, such as the wings and the body of the aircraft, the inspector is required to put on a safety harness and climb to the area of the aircraft to be visually inspected. This can be a dangerous endeavor, not only because of the slanted shape of some of the aircraft parts, but also because the inspector may be standing on the debris and lubricant that has accumulated on the outer surface of the structure during fastener installation and shaving. The debris and lubricant on the outer surface of the structure may be slick, and therefore, the inspector is at an increased risk of slipping during the visual inspection process.

Thus, there is a need in the industry for a technique for inspecting fasteners that are installed in structures without having to interrupt an automated fastener installation system in order to visually inspect each fastener. In addition, there is a need for such a fastener inspection technique that is safer and more efficient than the conventional technique that requires physically inspecting the parts of the structure in which the fasteners are installed by walking to the fasteners over debris and lubricant(s), which is a risky, time consuming and expensive process.

BRIEF SUMMARY OF THE INVENTION

The apparatus, method, and system for inspecting a fastener installed in a structure of the present invention provide an automated technique for quickly inspecting fasteners that are installed in structures, during the fastener installation process. Therefore, fasteners may be inspected without having to interrupt an automated fastener installation system in order to visually inspect each fastener. Because the fastener inspection technique that is provided via the present invention automatically inspects the fasteners during an automated fastener installation process, the technique is safer and more efficient than conventional fastener inspection techniques that require walking over debris and lubricant(s) to visually inspect installed fasteners.

The method for inspecting a fastener installed in a structure according to the present invention includes illuminating the fastener and a portion of the structure surrounding the fastener, detecting the light reflected from the fastener and the portion of the structure surrounding the fastener, analyzing the reflected light, and defining at least one inspection criteria. The apparatus and system for inspecting fasteners installed in a structure according to the present invention therefore include an illumination source for emitting the light that illuminates the fastener and a portion of the structure surrounding the fastener, and a sensor for detecting the reflected light. The sensor may also include a processing element for analyzing the reflected light and for defining the inspection criteria.

The structure has a coating that reflects light of a predefined wavelength differently than the fastener. As such, the light that illuminates the fastener and a portion of the structure surrounding the fastener has a wavelength within the predefined range. Embodiments of the present invention may also include a fastener that is at least partially made of a first material, and installed in a structure having at least an outer surface coating, which is at least partially made of a second material. Therefore, the light is reflected differently from the first material than from the second material, due to greater absorption of the light of the predefined bandwidth by one of the first and second materials.

The light reflected from the fastener and the portion of the structure surrounding the fastener is then detected and analyzed to determine an interface between exposed surfaces of the fastener and the coating that reflect the light differently. Based upon the detected interface, at least one inspection criteria may then be defined.

The present invention also includes a method of installing a fastener. In embodiments of the method for installing the fastener, the fastener, which is at least partially made of a first material, is inserted in a structure having an outer surface, which is at least partially made of a second material. A portion of the fastener that extends beyond the outer surface of the structure is then removed, and the fastener and the structure surrounding the fastener is illuminated with light of a predefined bandwidth. Due to the absorption of the light of the predefined bandwidth by one of the first and second materials, the light is reflected differently from the first material than from the second material. Based upon the differential reflection of the first and second materials, the interface between the first and second materials may be detected, and at least one inspection criteria may be identified based upon the interface.

The inspection criteria may be based upon a measurement of a dimension, a measurement of a diameter, and/or a measurement of a deviation from a circle of an exposed region of the fastener and adjacent portions of the structure from which the coating has been removed. In addition, a portion of the fastener may be shaved such that the portion is substantially in a plane that is common to the outer surface of the structure, and the amount of the fastener that is shaved may be adjusted based upon the inspection criteria. Embodiments of the present invention may also include storing the inspection criteria, such as in a storage element.

In one embodiment of the present invention, the emitted light may be between 650 and 675 nanometers. Embodiments of the present invention also may include light that is emitted at a light absorption frequency of one of the fastener and the coating. Furthermore, light emitting diodes may comprise the illumination source. Therefore, a plurality of light emitting diodes may be positioned proximate the fastener and the structure surrounding the fastener.

An image of the fastener and the portion of the structure surrounding the fastener may be captured. As such, the sensor may also include a device, such as a camera or a vision sensor, for capturing the image. The image, therefore, includes the interface between the exposed surfaces of the fastener and the coating that reflect light differently. In this embodiment of the present invention, the image may be displayed by a display screen. In addition, the inspection criteria may also be displayed.

A housing may surround at least a portion of the illumination source and sensor. As such, the housing has a lens that is aligned with the sensor, and at least one window aligned with the illumination source. To keep debris from accumulating on the lens, the window(s), the fastener, and the portion of the structure surrounding the fastener, a fluid source may be connected to the housing.

The various embodiments of the apparatus, method and system of the present invention therefore provide an efficient and safe technique for inspecting a fastener installed in a structure. Because the inspection technique is automated, it may be integrated into an automated fastener installation device, such that the fastener may be inspected immediately after it is installed in the structure. This inspection technique is also less labor intensive and time consuming, and therefore, less expensive, than the conventional inspection technique that requires visual inspection of the installed fasteners.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

The apparatus, method, and system for inspecting a fastener installed in a structure of the present invention provide an automated technique for inspecting fasteners that are installed in structures quickly, and during the fastener installation process. Therefore, fasteners may be inspected without having to interrupt an automated fastener installation system in order to visually inspect each fastener. Because the fastener inspection technique that is provided via the present invention automatically inspects the fasteners during an automated fastener installation process, the technique is safer and more efficient than conventional fastener inspection techniques that require walking over debris and lubricant(s) to visually inspect installed fasteners.

The portion of a fastener that extends beyond the structure in which it is installed, may be removed in order to create a smooth outer surface of the structure. A smooth outer surface of a structure may be desired in various applications for many reasons. For instance, a smooth outer surface may be desired for aerodynamic reasons, aesthetic reasons, structural integrity, and/or any other reason known to those skilled in the art. The portion of the fastener that extends beyond the structure may be removed by shaving the portion of the installed fastener until the outer surface of the fastener is substantially flush with the outer surface of the structure.

Figure 1:
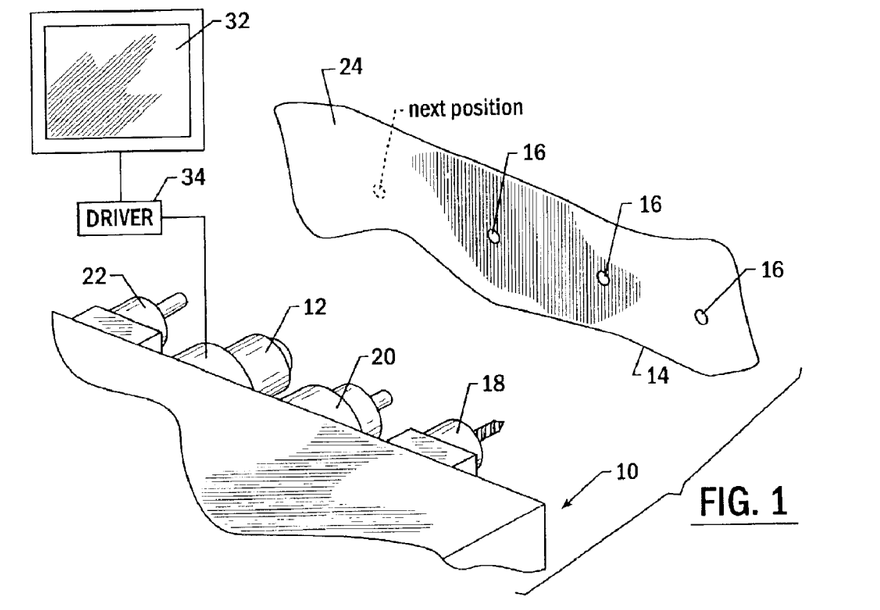
FIG. 1 is a perspective view of a fastener installation system that includes an apparatus for inspecting a fastener installed in a structure, according to one embodiment of the present invention.

A fastener installation system, such as a 777 Automated Wing Assembly System, commercially available from the General Electro Mechanical Corporation, may be utilized in aerospace applications, and may both install fasteners and shave the installed fasteners, as described above. FIG. 1 illustrates one embodiment of a fastener installation system 10 that includes a fastener inspection apparatus 12, which is described in detail hereinbelow. The fastener installation system 10 is capable of moving relative to a structure 14, into which the fastener installation system 10 can install at least one fastener 16. The fastener installation system 10 can automatically drill a hole in a desired location on a structure, such as with a drill motor 18. The fastener installation system 10 is then capable of moving in order to align a fastener installing device 20 with the drilled hole, such that the fastener installing device 20 inserts the fastener 16 in the drilled hole. In addition, the fastener installing device 20 may perform any other action on the inserted fastener in order to install the fastener 16 in the structure 14. For instance, if the fastener 16 is a rivet, the rivet may also be formed by the fastener installing device 20. Once the fastener 16 is installed in the structure 14, the fastener installation system 10 is capable of moving in order to align a shaving spindle 22 with the fastener 16, such that the shaving spindle 22 can shave the portion of the fastener 16 that extends beyond the outer surface of the structure 14. After the fastener 16 is shaved, the fastener installation system 10 moves in order to align the drill motor 18 with the next area of the structure 14 that is to receive a fastener 16, and the process described above is carried out again.

The structure 14 typically includes a coating 24 that at least partially covers the outer surface of the structure 14. In one embodiment of the present invention, the coating 24 is a layer of paint, such as primer, that is approximately 0.002 inches thick. The coating 24 and the fastener 16 reflect light of a predefined wavelength differently. As used herein, the different reflection of light of a predetermined wavelength includes situations in which light of the predetermined wavelength is absorbed differently by the coating 24 and the fastener 16, including, for example, the situation in which light of the predetermined wavelength is reflected by one of the coating 24 and the fastener 16, while the light is completely absorbed by the other of the coating 24 and the fastener 16. In this latter scenario in which the light is completely absorbed by either the fastener or the coating, the frequency of the light is considered to be at the light absorption frequency of one of the fastener or the coating and, most typically, the coating. Thus, the fastener 16 is typically made of a metallic material, such as aluminum and/or titanium, but the fastener 16 may also be made of non-metallic materials, such as non-metallic composite materials, thermoplastic, and/or nylon. The coating 24, therefore, reflects light differently than the metallic and/or non-metallic material from which the fastener is made. For instance, in one embodiment of the present invention, the coating 24 is a light green and/or yellow layer of primer paint, and the fastener 16 is made of aluminum. The light green and/or yellow layer of primer paint reflects light in the range of 650 to 675 nanometers differently than aluminum, such that the primer paint absorbs the light, while the aluminum reflects the light. In further embodiments of the present invention, at least the surface of the structure 14 below the coating 24 may also be made of aluminum. In addition, in embodiments of the present invention in which the structure 14 is a segment of an aircraft, the outer surface of the structure below the coating may have small recessed dimples, known as a "shot peened" surface to those skilled in the art, that also generally reflects light differently than the coating.

Figure 2A:
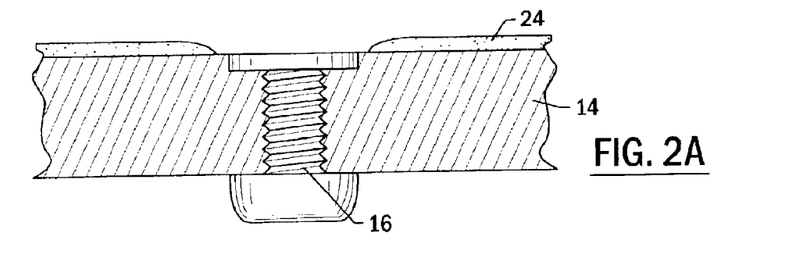
FIGS. 2A and 2B illustrate a cross-sectional view and top planar view, respectively, of a fastener, a portion of which has been removed, such that the outer surface of the fastener is substantially in a plane that is common to the outer surface of the structure, and a portion of the coating on the surface has been removed, according to one embodiment of the present invention.
Figure 2B:
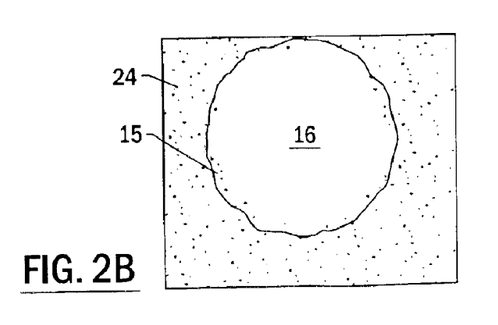

In removing the portion of the fastener 16 that extends beyond the structure 14, such that the outer surface of the fastener is substantially flush with the outer surface of the structure, the shaving spindle 22 may at least partially remove a portion of the coating 24 surrounding the fastener 16. FIGS. 2A and 2B illustrate a cross-sectional view and a top planar view, respectively, of one embodiment of the fastener 16 and the structure 14 surrounding the fastener when the fastener has been shaved to the proper height, such that the outer surface of the fastener is substantially flush with the outer surface of the structure 14, i.e., a good shave. FIG. 2A demonstrates that the outer surfaces of the fastener 16 and the structure 14 are substantially in a common plane. FIG. 2B shows that the top view of the fastener 16 and structure 14 includes the coating 24 being partially removed from the structure, such that a portion of the structure 14 under the coating is partially exposed, which is shown in FIG. 2B as a portion of the shot peened surface 15 of the structure 14. Thus, the edge between the structure 14 and the coating 24 is not well-defined. In other embodiments of the present invention, all of the coating 24 that comes into contact with the shaving spindle 22 may be removed without removing any or at least without removing a significant portion of the structure 14, such that there is a well-defined edge between the structure 14 and the coating 24, with the shot peened surface 15 of the structure 14 exposed about the periphery of the fastener.

Figure 3A:
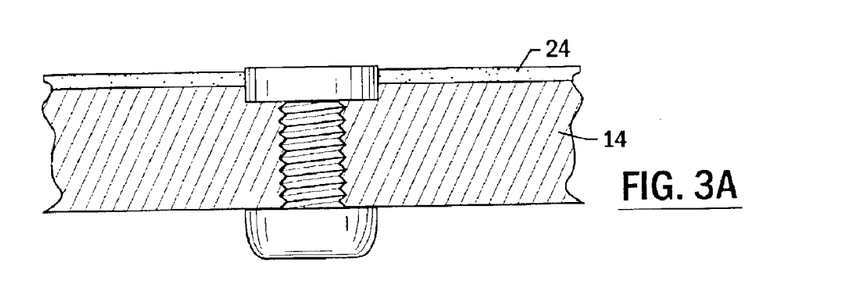
FIGS. 3A and 3B illustrate a cross-sectional view and top planar view, respectively, of a fastener that extends beyond the outer surface of a structure, according to one embodiment of the present invention.
Figure 3B:
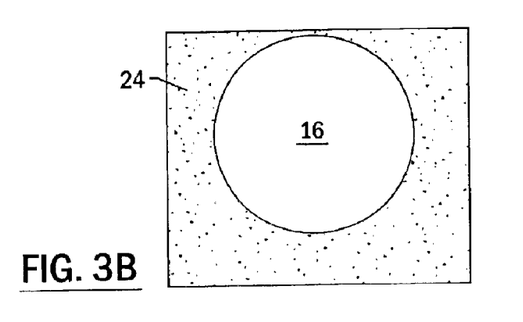

FIGS. 3A and 3B, however, illustrate a cross-sectional view and a top planar view, respectively, of embodiments of a fastener 16 and structure 14 when the shaving spindle 22 has not removed a sufficient portion of the fastener 16, i.e., a high shave. FIG. 3A demonstrates that a portion of the fastener 16 extends beyond the outer surface of the structure 14, even after the shaving spindle 22 has shaved the fastener 16. FIG. 3B shows the top view of the fastener 16, the outer edge of which is well-defined in relation to the structure 14. The outer edge of the top view of the fastener 16, therefore has the same diameter as the top of the fastener 16. To correct the high shave situation, the portion of the fastener 16 that extends beyond the structure 14 is shaved further until the outer surfaces of the fastener 16 and the structure 14 are substantially in a common plane, as shown in FIGS. 2A and 2B. The shaving spindle 22 may be utilized for the further shaving, or the shaving may be done by hand, such as with any type of electric, electro-mechanical, or manual shaving device.

Figure 4A:
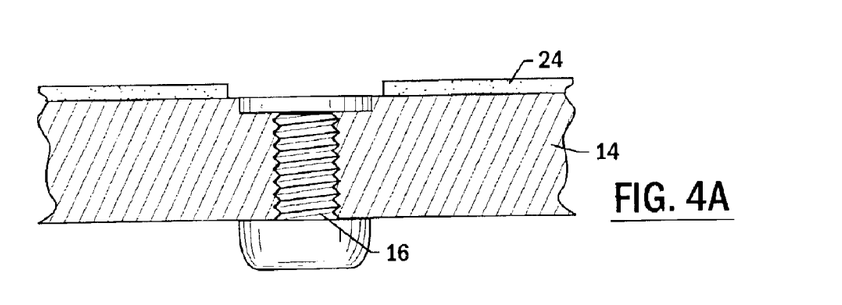
FIGS. 4A and 4B illustrate a cross-sectional view and top planar view, respectively, of a fastener, a portion of which has been removed, such that the outer surface of the fastener and a portion of the structure surrounding the fastener create a recessed region in the structure, according to one embodiment of the present invention.
Figure 4B:
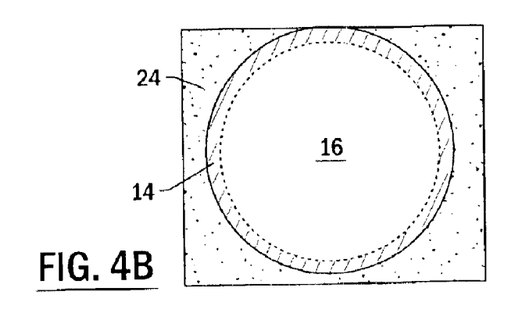

If a fastener 16 has been shaved too much, i.e. a low shave, however, the shaving spindle 22 will shave not only the fastener 16, but also a portion of the structure 14 surrounding the fastener 16, as shown in FIGS. 4A and 4B. As such the portion of the structure 14 surrounding the fastener 16, along with the shaved fastener 16, generally create a recessed area in the structure 14, illustrated by FIG. 4A. The recessed area in the structure 14, therefore, has a diameter that is the same as the diameter of the shaving spindle 22, which is a diameter that is larger than the diameter of the top portion of the fastener 16. The top view of the fastener 16 and structure 14 in FIG. 4B shows that the outer edge of the recessed portion of the structure 14 is well-defined at least partially due to the removal of the coating 24 and the outer surface of the structure from the portion of the structure 14 surrounding the fastener 16. Thus, the contrast between the coating 24 and the material of the recessed area in the structure 14, and the difference in the height of the recessed area to the rest of the structure, provide a well-defined edge between the recessed area and the rest of the structure. In embodiments of the present invention in which the surface of the structure 14 directly below the coating 24 has a shot peened texture, the shot peen texture is removed from the recessed area in the structure 14. To correct the low shave situation, the recessed area is filled and blended to create a smooth outer surface of the structure 14.

Furthermore, if the base of the shaving spindle 22 is not substantially parallel to the top of the fastener 16, and/or if the fastener 16 is not installed properly installed in the structure 14, then the shaved fastener may be a combination of the shaved fasteners shown in FIGS. 2A and B, 3A and B, and 4A and B. For example, part of the fastener 16 may be shaved properly, while the other part is left too high or too low.

Figure 5:
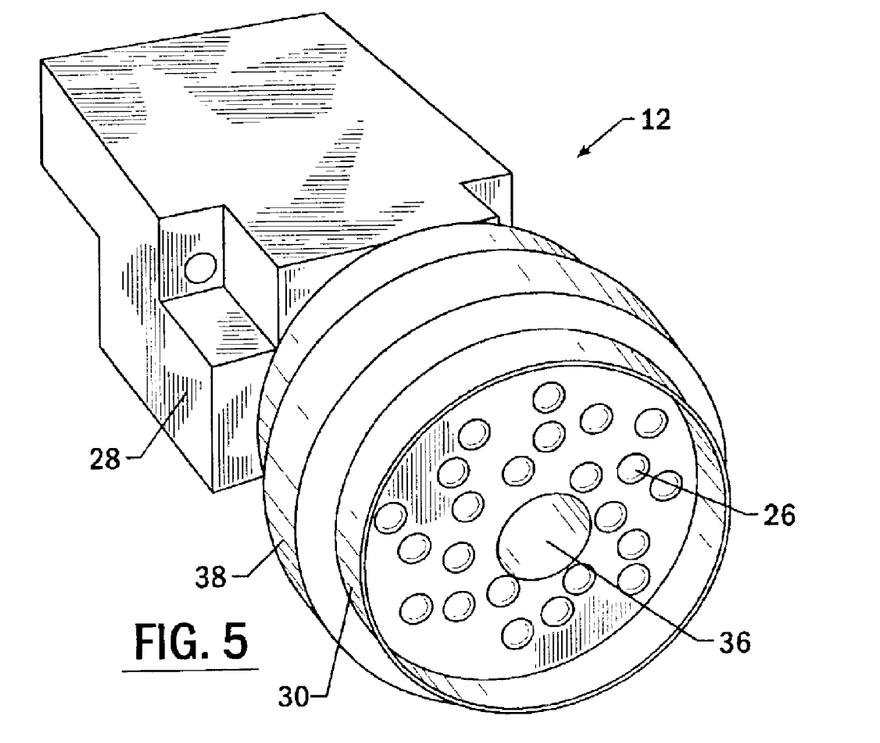
FIG. 5 is a perspective view of a sensor, illumination source, and a housing of an apparatus for inspecting a fastener installed in a structure, according to one embodiment of the present invention.

In order to determine whether a shaved fastener 16 has been shaved properly, high, and/or low, the shaved fastener 16 is inspected. As such, a fastener inspection apparatus 12 may be utilized to analyze the shaved fastener 16 and at least a portion of the surrounding structure 14. One embodiment of a fastener inspection apparatus 12 of the present invention is shown in FIG. 5. The fastener inspection apparatus 12 of the present invention includes an illumination source 26 and a sensor 28. In embodiments of the fastener inspection apparatus 12 of the present invention, the illumination source 26 and the sensor 28 may be located within a housing 30. The housing 30 provides alignment and protection for the illumination source 26 and the sensor 28, in addition to providing a surface on which to mount other desired components, as explained further hereinbelow.

The illumination source 26 is capable of emitting light of a predefined wavelength to illuminate the fastener 16 and the portion of the structure surrounding the fastener. In advantageous embodiments of the present invention, the predefined wavelength is the wavelength or the range of wavelengths in which a fastener 16 reflects light differently than a coating 24 on the structure 14. For example, in embodiments of the present invention in which the coating 24 on the structure is a light green and/or yellow paint, the illumination source 26 may emit light between 650 and 675 nanometers, which is the absorption frequency of the light green and/or yellow paint. As such, the light green and/or yellow paint absorbs light having a frequency of 650 to 675 nanometers, but other colors reflect light in the 650 to 675 nanometer range. The effect of emitting light only at the absorption frequency of one of the colors of either the coating or the fastener results in that color being blacked out, i.e., not reflected, which isolates or highlights the reflection of the light by the other one of the coating or the fastener. FIGS. 2B, 3B, and 4B illustrate embodiments of the blacking out or lack of reflection from the light green and/or yellow paint coating when light having a frequency of 650 to 675 nanometers is emitted by the illumination source 26. These figures also illustrate that the fastener 16 and any of the structure 14 from which the coating has been removed reflect the light, which isolates the non-coated areas against a black background. As will be noted below, the fastener and those portions of the structure from which the coating has been removed may reflect the light somewhat differently to permit further discrimination of the fastener.

As illustrated in the embodiment of the fastener inspection apparatus 12 shown in FIG. 5, the illumination source 26 may include a plurality of light emitting diodes (LEDs). LEDs may be selected that emit light of a particular wavelength or range of wavelengths. As such, LEDs may be selected that emit light at the absorption frequency of one of the items that are to be illuminated, such as based upon the color of the coating. To determine the absorption frequency of a color, such as the color of the coating, an instrument that measures the spectral radiance of a color may be utilized. For instance, a Photo Research PR 715 Spectraradiometer may be used to determine the absorption frequency of a color. The LEDs' frequency output is a function of the current supplying the LEDs. As such, the illumination source may include an LED driver to regulate the current flow to the LEDs, such that the LEDs' frequency output remains at a desired wavelength or range of wavelengths.

The LEDs also may be positioned in any manner that creates an advantageous illumination of the fastener 16 and at least a portion of the structure 14 surrounding the fastener. As illustrated in the embodiment of the fastener inspection apparatus 12 of FIG. 5, the LEDs may be spaced apart about a longitudinal axis of the fastener inspection apparatus in order to obtain substantially even illumination of the fastener 16 and the portion of the structure 14 surrounding the fastener. The LEDs may be positioned in other manners, however, to provide any other desired type of illumination.

In embodiments of the fastener inspection apparatus 12 of the present invention that include a housing for at least the illumination source 26 and the sensor 28, the illumination source 26 may be mounted within the housing 30, and at least one window may be aligned with the illumination source. For instance, in the embodiment of the fastener inspection apparatus 12 of the present invention shown in FIG. 5, the LEDs are mounted within the housing 30, and windows in the housing 30 are aligned with the individual LEDs to permit the LEDs to emit light out of the housing 30, while also protecting the LEDs.

The sensor 28 detects the light that is reflected from the fastener 16 and the portion of the structure 14 surrounding the fastener 16. The sensor 28 also analyzes the reflected light to determine an interface between exposed surfaces of the fastener 16 and the coating 24 that reflect the light differently. Thus, the sensor 28 includes a processing element, such as a microprocessor or the like, that may be located within the sensor 28, within the housing 30, and/or it may be located remotely from the sensor 28. The processing element is in communication with the sensor via any type of connection known to those skilled in the art, such as a direct electrical or a wireless connection. In one embodiment of the fastener inspection apparatus, method and system of the present invention, the sensor 28 is a Series 600 SmartImage sensor commercially available from Dickerson Vision Technology (DVT). This sensor uses a Charged Coupled Device (CCD) and a processing element located within the sensor.

The sensor 28 also may include a device, such as a camera or a vision sensor, for capturing an image of the fastener 16 and the portion of the structure 14 surrounding the fastener, including the interface between the exposed surfaces of the fastener 16, the structure 14 and/or the coating 24. In addition, the sensor 28 may be in communication with a network, such as a local area network (LAN), wide area network (WAN), an intranet, the Internet, or any other type of conventional or wireless network. Thus, any type of computing element or peripheral, such as a storage element and/or a display element may be in communication with the sensor 28 via the network and/or directly. Thus, the sensor 28 may transmit analysis data and/or images to any other computing element in communication with the sensor, such as for storage, data acquisition, display and/or further analysis. Furthermore, the other computing element(s) that are in communication with the sensor 28 may transmit data to the sensor 28. For example, one or more of the computing elements in communication with the sensor 28 may transmit algorithms, programs, and or any other type of instructions to the processing element of the sensor. In other embodiments of the fastener inspection apparatus of the present invention, software or other types of updates or additions to the processing element may be transmitted to the sensor 28.

As discussed above, and as shown in FIG. 1, the sensor 28 may be in communication with a display element 32. As such, the display element 32 may display the images captured by the device, such as a camera or vision sensor, or any other data that is transmitted and/or received by the sensor 28. The display element 32 may be part of a conventional computer system having a video card, as known to those skilled in the art. Alternatively, the display element 32 may operate independently of a computer, such that the display element 32 is in direct communication with the sensor 28 via a display driver 34, which provides an interface between the sensor 28 processing element and the display element 32.

In addition, the sensor 28 is capable of defining at least one inspection criteria based upon the interface between exposed surfaces of the fastener 16 and the coating 24 that reflect light differently. As such, the processing element of the sensor 28 may store or be capable of accessing at least one inspection algorithm. The inspection algorithm(s) are therefore used to evaluate the various data and/or images that the sensor 28 receives via the light reflected from the fastener 16 and the portion of the structure surrounding the fastener, which is detected by the sensor 28. The inspection algorithm(s) define at least one inspection criteria regarding the inspection of the fastener. An inspection algorithm may be any type of directions regarding the manipulation of the data and/or images received by the sensor 28, as known to those skilled in the art. In one embodiment of the fastener inspection apparatus, method and system of the present invention, an inspection algorithm may be a routine implemented by a software program, and the routine may include a plurality of subroutines, i.e., scripts, that evaluate specific inspection data and/or images.

The inspection criteria may be any type of result that is obtained from the analysis of the interface. For instance, in one embodiment of the fastener inspection apparatus of the present invention, the inspection criteria is based upon a measurement of a dimension of an exposed region of the fastener 16 and adjacent portions of the structure 14 from which the coating 24 has been removed. Thus, the sensor 28 may measure a diameter, circumference, and/or any other dimension of the exposed regions of the fastener 16 and adjacent portions, if any, of the structure 14 from which the coating has been removed. An inspection algorithm is then capable of evaluating the dimension measurement in order to determine certain characteristics of the fastener, such as whether the fastener has a low shave or high shave. For instance, with respect to FIGS. 3B and 4B, the inspection algorithm may evaluate a diameter measurement of the area that reflects light, i.e., is not blacked out. As such, a diameter of this area that matches the diameter of the top of the fastener indicates that the fastener has a high shave, as shown in FIG. 3B, while a diameter that is larger then the diameter of the top of the fastener, such as a diameter that is equal to the diameter of the shaving portion of the shaving spindle 22, indicates that the fastener has a low shave, as shown in FIG. 4B.

Other embodiments of the inspection criteria utilized by the fastener inspection apparatus of the present invention may also be based upon a measurement of the standard deviation of the interface between an exposed region (generally constituting the fastener and adjacent portions of the structure from which the coating 24 has been removed) and the coating from a circular shape. In one embodiment of the fastener inspection apparatus, system and method of the present invention, the sensor 28 may extract edge points about the interface, in order to determine the standard deviation. In particular, the inspection algorithm may evaluate the edge points and calculate the radius of the exposed region and the center point of the exposed region. The inspection algorithm also calculates the deviation of the shape of the interface as defined by the edge points from a best fit circle to determine the standard deviation of the exposed region. In the examples described above regarding FIGS. 2A, 2B, 3A, 3B, 4A, and 4B, and the high, low or proper shave of a fastener, high and low shaves result in a low standard deviation because the edge of the exposed region is well-defined such that the shape of the exposed region is very similar to a best fit circle, as illustrated in FIGS. 3B and 4B. In contrast, proper shaves result in a high standard deviation because the edge of the exposed region is not well-defined due to the partial removal of the coating 24 from the structure 14 such that the shape of the exposed region is not similar to a best fit circle, as illustrated in FIG. 2B. In other embodiments of the fastener inspection apparatus, system and method of the present invention, the standard deviation may be determined in any other manner known to those skilled in the art. In addition to, or as an alternative to, determining the standard deviation of the exposed region, an inspection algorithm may determine an index of eccentricity and/or the compactness of the exposed region. In embodiments of the fastener inspection apparatus, method and system of the present invention that evaluate the exposed region to determine an index of eccentricity, a fastener with a low or high shave will have a high index of eccentricity, and a fastener with a proper shave will have a low index of eccentricity.

From the inspection criteria described above, an exposed region that has a diameter that is larger than the diameter of the top of the fastener, such as a diameter that is equal to the diameter of the shaving portion of the shaving spindle 22, and a low standard deviation and/or a high index of eccentricity, is a fastener with a low shave. An exposed region that has a diameter that is equal to the diameter of the top of the fastener, and a low standard deviation and/or a high index of eccentricity, is a fastener with a high shave. Finally, an exposed region that has a high standard deviation and/or a low index of eccentricity, is a fastener with a proper shave. In addition, the exposed region may include combinations of the above, such that part of the fastener has a high or low shave, while the other part is properly shaved. The inspection algorithm(s) may also be capable of evaluating these fasteners based upon a combination of the techniques described above. When an operator of a fastener inspection system receives the feedback regarding the shaving of the fastener, then the operator may adjust the shaving spindle 22 accordingly if the fasteners are not being shaved properly.

The sensor 28 may also be mounted within the housing 30 in order to protect the sensor and/or align the sensor with the illumination source 26. The housing 30 therefore includes an opening 36 in which a lens may be positioned to prevent any debris, dust or other unwanted material from entering the housing 30 and obstructing the function of the sensor 28.

The fastener inspection apparatus 12 may be mounted to a fastener installation system 10, one embodiment of which is shown in FIG. 1. As described hereinabove, the fastener installation system 10 drills a hole in the structure 14 with a drill motor 18, installs a fastener 16 into the drilled hole with a fastener installing device 20, then shaves the portion of the fastener 16 that extends beyond the outer surface of the structure, such as with a shaving spindle 22. As such, the fastener installation system 10 is capable of moving in order to align the appropriate component that is mounted to the system 10 with the desired location on the structure 14. The fastener inspection apparatus 12, therefore, also may be mounted to the fastener installation system 10 in order to inspect the fastener 16 and a portion of the structure 14 surrounding the fastener. In the embodiment of the fastener installation system 10 shown in FIG. 1, the fastener inspection apparatus 12 is mounted between the fastener installing device 20 and the shaving spindle 22. As such, after the shaving spindle finishes shaving the fastener 16, and the fastener installation system 10 moves to align the drill motor 18 with the next area on the structure 14 to be drilled, the fastener inspection apparatus 12 passes over the shaved fastener. In other embodiments of the fastener installation system 10, the fastener inspection apparatus 12 may be positioned in other locations upon the fastener installation system, so long as the fastener installation system moves over the shaved fastener at any time after the fastener has been shaved.

As the fastener inspection apparatus 12 passes over the shaved fastener, it illuminates the fastener and the portion of the structure surrounding the fastener, and it detects the reflected light. The fastener inspection apparatus 12 may also capture an image of the fastener and portion of the structure surrounding the fastener, perform the analysis and define the inspection criteria, as described in detail hereinabove, as the fastener inspection apparatus 12 moves over the shaved fastener. As such, in preferred embodiments of the fastener inspection apparatus 12 of the present invention, the speed of the processing element of the sensor 28 should be fast enough to detect all of the desired data from the illuminated portion of the fastener and structure, and to perform the desired analysis, without affecting the speed of the fastener installation system 10.

The fastener installation system 10 may also include at least one source of lubricant and/or coolant that is proximate to the shaving spindle 22, and that may be may be applied to the fastener 16 and/or the shaving spindle 22 in order to shave a portion of the fastener without creating significant amounts of friction and heat, which could be detrimental to the structure, fastener, and/or shaving spindle 22. As the fastener 16 is shaved, the portion of the fastener that is removed may create debris that mixes with the lubricant and/or coolant, hereinafter "contaminants," and disperses about the shaving spindle 22. Thus, the contaminants may land on the other components of the fastener installation system 10, including the fastener inspection apparatus 12. If the contaminants land on the fastener inspection apparatus 12 and obstruct the sensor 28 and/or illumination source 26, then the sensor's detection of reflected light and/or the image of the structure obtained by the sensor 28 may be an incorrect representation of the fastener and the portion of the structure surrounding the fastener. As such, the housing 30 of the fastener inspection apparatus 12 may also include a fluid source 38, as shown in the embodiment of the fastener inspection apparatus 12 of FIG. 5. The fluid source 38 is positioned relative to the lens that is aligned with the sensor 28 and the window(s) that are aligned with the illumination source 26, in order to prevent the contaminants from landing on the lens, the window(s), the fastener, and/or the portion of the structure surrounding the fastener. Thus, the fluid source 38 guides the contaminants away from the lens and window(s) of the housing 30 and away from the fastener and the portion of the structure surrounding the fastener, which are in the line of view of the sensor 28. In one embodiment of the fastener installation apparatus, method and system of the present invention, the fluid source constantly forces air in a direction away from the lens and/or window(s) in order to guide the contaminants away from the lens and/or window(s). In this embodiment, direction of the air also guides contaminants away from the fastener and the portion of the structure surrounding the fastener. In other embodiments of the fastener installation apparatus, method and system of the present invention, the fluid source may utilize various other fluids, such as water and/or any other liquid or gas, to similarly redirect the contaminants.

Because the contaminants, such as the lubricants and/or coolants described above, may contain chemicals, such as isopropyl alcohol, that may be harmful or corrosive, as known to those skilled in the art, the housing 30 of the fastener installation apparatus 12 is advantageously made of a material that is impervious to the chemicals contained in the contaminants. Therefore, in one embodiment of the housing 30, the housing 30 is made of an epoxy resin and is painted with an epoxy-based paint that is impervious to the isopropyl alcohol contained in the spray lubricant that is used on the shaving spindle 22. The housing 30, however, may be made of other materials depending upon the contaminants, if any, utilized in the specific application of the fastener inspection apparatus 12.

The various embodiments of the apparatus, method and system of the present invention therefore provide an efficient and safe technique for inspecting a fastener installed in a structure. Because the inspection technique is automated, it may be integrated into an automated fastener installation device, such that the fastener may be inspected immediately after it is installed in the structure. This inspection technique is also less labor intensive and time consuming, and therefore, less expensive, than the conventional inspection technique that requires visual inspection of the installed fasteners.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An apparatus for inspecting a fastener installed in a structure, wherein the fastener reflects light of a predefined range of wavelengths differently than a coating on the structure, the apparatus comprising:
    an illumination source that emits light for illuminating the fastener and a portion of the structure surrounding the fastener, with light having a wavelength within the predefined range; and
    a sensor for detecting light reflected from the fastener and the portion of the structure surrounding the fastener, said sensor comprising a processing element for analyzing the reflected light to determine an interface between exposed surfaces of the fastener and the coating that differently reflect the light, wherein the processing element is also capable of defining at least one inspection criteria based upon the interface.

2. The apparatus according to claim 1, further comprising a housing surrounding at least portions of said sensor and said illumination source, wherein said housing comprises a lens aligned with said sensor, and at least one window aligned with said illumination source.

3. The apparatus according to claim 2, further comprising a fluid source connected to said housing for preventing debris from accumulating on at least one of the lens, the at least one window, the fastener, and the portion of the structure surrounding the fastener.

4. The apparatus according to claim 1, wherein said sensor further comprises a device for capturing an image of the fastener and the portion of the structure surrounding the fastener, including the interface between the exposed surfaces that differently reflect the light.

5. The apparatus according to claim 4, further comprising a display for displaying the image of the fastener and the portion of the structure surrounding the fastener, and for displaying the inspection criteria.

6. The apparatus according to claim 1, wherein the processing element defines the inspection criteria based upon a measurement of a dimension of an exposed region of the fastener and adjacent portions of the structure from which the coating has been removed.

7. The apparatus according to claim 1, wherein the processing element defines the inspection criteria based upon a measurement of a diameter of an exposed region of the fastener and adjacent portions of the structure from which the coating has been removed.

8. The apparatus according to claim 1, wherein the processing element defines the inspection criteria based upon a measurement of a deviation of an exposed region of the fastener and adjacent portions of the structure from which the coating has been removed from a circular shape.

9. The apparatus according to claim 1, wherein said illumination source comprises a plurality of light emitting diodes.

10. The apparatus according to claim 1, wherein said illumination source emits light at a light absorption frequency of one of the fastener and the coating.

11. The apparatus according to claim 1, wherein said illumination source emits light between 650 and 675 nanometers.

12. A method for inspecting a fastener installed in a structure, wherein the fastener reflects light of a predefined range of wavelengths differently than a coating on the structure, the method comprising:
    illuminating the fastener and a portion of the structure surrounding the fastener, with light having a wavelength within the predefined range;
    detecting light reflected from the fastener and the portion of the structure surrounding the fastener;
    analyzing the reflected light to determine an interface between exposed surfaces of the fastener and the coating that differently reflect the light; and
    defining at least one inspection criteria based upon the interface.

13. The method according to claim 12, wherein a portion of the fastener is shaved such that the portion is substantially in a plane that is common to an outer surface of the structure, and further comprising adjusting an amount of the fastener that is shaved based upon the inspection criteria.

14. The method according to claim 12, wherein illuminating a portion of the structure comprises positioning a plurality of light emitting diodes proximate the fastener and the structure surrounding the fastener.

15. The method according to claim 12, wherein illuminating a portion of the structure comprises emitting light at a light absorption frequency of one of the fastener and the coating.

16. The method according to claim 12, wherein illuminating a portion of the structure comprises emitting light between 650 and 675 nanometers.

17. The method according to claim 12, further comprising capturing an image of the fastener and the structure surrounding the fastener, including the interface between exposed surfaces of the fastener and the coating based upon the differently reflected light.

18. The method according to claim 17, further comprising displaying the image of the fastener and the structure surrounding the fastener, and the inspection criteria subsequent to capturing the image of the fastener and the structure surrounding the fastener.

19. The method according to claim 12, wherein defining at least one inspection criteria comprises measuring at least one dimension of an exposed region of the fastener and adjacent portions of the structure from which the coating has been removed.

20. The method according to claim 12, wherein defining at least one inspection criteria comprises measuring a diameter of an exposed region of the fastener and adjacent portions of the structure from which the coating has been removed.

21. The method according to claim 12, wherein defining at least one inspection criteria comprises measuring a deviation of the shape of an exposed region of the fastener and adjacent portions of the structure from which the coating has been removed from a circular shape.

22. A method for inspecting a fastener at least partially made of a first material, and installed in a structure having at least an outer surface coating at least partially made of a second material, comprising:
   illuminating a portion of the structure, wherein the portion comprises the fastener and a portion of the structure surrounding the fastener, wherein illuminating comprises emitting light of a predefined bandwidth;
   differently reflecting the light from the first material and the second material due to greater absorption of the light of the predefined bandwidth by one of the first and second materials;
   detecting an interface between the first and second materials based upon the different reflection from the first and second materials; and
   defining at least one inspection criteria based upon the detected interface.

23. The method according to claim 22, wherein a portion of the fastener is shaved such that the portion is substantially in a plane that is common to the outer surface of the structure, and further comprising adjusting an amount of the fastener that is shaved based upon the inspection criteria.

24. The method according to claim 22, wherein illuminating a portion of the structure comprises positioning a plurality of light emitting diodes proximate the fastener and the structure surrounding the fastener.

25. The method according to claim 22, wherein illuminating a portion of the structure comprises emitting light at a light absorption frequency of one of the first material and second material.

26. The method according to claim 22, wherein illuminating a portion of the structure comprises emitting light between 650 and 675 nanometers.

27. The method according to claim 22, further comprising capturing an image of the fastener and the structure surrounding the fastener, including the interface between the first and second materials based upon the differently reflected light.

28. The method according to claim 27, further comprising displaying the image of the fastener and the structure surrounding the fastener, and the inspection criteria subsequent to capturing the image of the fastener and the structure surrounding the fastener.

29. The method according to claim 22, wherein defining at least one inspection criteria comprises measuring at least one dimension of an exposed region of the fastener and adjacent portions of the structure from which the coating has been removed.

30. The method according to claim 22, wherein defining at least one inspection criteria comprises measuring a diameter of an exposed region of the fastener and adjacent portions of the structure from which the coating has been removed.

31. The method according to claim 22, wherein defining at least one inspection criteria comprises measuring a deviation of the shape of an exposed region of the fastener and adjacent portions of the structure from which the coating has been removed from a circular shape.

32. A system for inspecting a fastener at least partially made of a first material, and installed in a structure having an outer surface coating at least partially made of a second material, comprising:
   an illumination source capable of emitting light in a predefined bandwidth to illuminate the fastener and a portion of the structure surrounding the fastener and to be differently reflected therefrom due to the absorption of the light of the predefined bandwidth by one of the first and second materials; and
   a sensor for capturing the light reflected from the fastener and the portion of the structure surrounding the fastener, said sensor comprising a processing element for detecting an interface between the first and second materials based upon differential reflection by the first and second materials, said processing element also capable of defining at least one inspection criteria based upon the interface between the first and second materials.

33. The system according to claim 32, wherein a portion of the fastener is shaved such that the portion is substantially in a plane that is common to the outer surface of the structure, and wherein said processing element is also capable of adjusting an amount of the fastener that is shaved based upon the inspection criteria.

34. The system according to claim 32, wherein said illumination source comprises a plurality of light emitting diodes capable of being positioned proximate the fastener and the structure surrounding the fastener.

35. The system according to claim 32, wherein said illumination source is capable of emitting light at a light absorption frequency of one of the fastener and the coating.

36. The system according to claim 32, wherein said illumination source is further capable of emitting light between 650 and 675 nanometers.

37. The system according to claim 32, wherein said sensor is also capable of capturing an image of the fastener and the structure surrounding the fastener, including the interface between the first and second materials.

38. The system according to claim 37, further comprising a display element capable of displaying the image of the fastener and the structure surrounding the fastener, and the inspection criteria.

39. The system according to claim 32, wherein the processing element is also capable of defining the inspection criteria based upon a measurement of a dimension of an exposed region of the fastener and adjacent portions of the structure from which the coating has been removed.

40. The system according to claim 32, wherein said processing element is also capable of defining the inspection criteria based upon a measurement of a diameter of an exposed region of the fastener and adjacent portions of the structure from which the coating has been removed.

41. The system according to claim 32, wherein said processing element is also capable of defining the inspection criteria based upon a measurement of a deviation of an exposed region of the fastener and adjacent portions of the structure from which the coating has been removed, from a circular shape.

42. The system according to claim 32, further comprising a storage element capable of storing the inspection criteria.

43. A method for installing a fastener, comprising:
   inserting the fastener in a structure, wherein the fastener is at least partially made of a first material, and wherein the structure has an outer surface at least partially made of a second material;

removing a portion of the fastener that extends beyond the outer surface of the structure;

illuminating a portion of the structure including the fastener and the structure surrounding the fastener with light of a predefined bandwidth;

differentially reflecting the light from the first material and the second material due to the absorption of light of the predefined bandwidth by one of the first and second materials;

detecting an interface between the first and second materials based upon the differential reflection of the first and second materials; and identifying at least one inspection criteria based upon the detected interface.

44. The method according to claim 43, further comprising adjusting the portion of the fastener that is removed based upon the identified inspection criteria.

45. The method according to claim 43, wherein illuminating a portion of the structure comprises positioning a plurality of light emitting diodes proximate the fastener and the structure surrounding the fastener.

46. The method according to claim 43, wherein illuminating a portion of the structure comprises emitting light at a light absorption frequency of one of the first material and the second material.

47. The method according to claim 43, wherein illuminating a portion of the structure comprises emitting light between 650 and 675 nanometers.

48. The method according to claim 43, further comprising capturing an image of the fastener and the structure surrounding the fastener, including the interface between the first and second materials based upon the differently reflected light.

49. The method according to claim 48, further comprising displaying the image of the fastener and the structure surrounding the fastener, and the inspection criteria subsequent to capturing the image of the fastener and the structure surrounding the fastener.

50. The method according to claim 43, wherein identifying at least one inspection criteria comprises measuring at least one dimension of an exposed region of the fastener and adjacent portions of the structure from which the coating has been removed.

51. The method according to claim 43, wherein identifying at least one inspection criteria comprises measuring a diameter of an exposed region of the fastener and adjacent portions of the structure from which the coating has been removed.

52. The method according to claim 43, wherein identifying at least one inspection criteria comprises measuring a deviation of the shape of an exposed region of the fastener and adjacent portions of the structure from which the coating has been removed, from a circular shape.

* * * * *